US010653547B2

(12) United States Patent
Vollbrecht et al.

(10) Patent No.: US 10,653,547 B2
(45) Date of Patent: May 19, 2020

(54) TRUNK ORTHOSIS (71) Applicant: OTTO BOCK HEALTHCARE GMBH, Duderstadt (DE)

(72) Inventors: Matthias Vollbrecht, Herzberg (DE); Klaus Lidolt, Duderstadt (DE); Alexander Von Ascheberg, Duderstadt (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 538 days.

(21) Appl. No.: 15/117,693

(22) PCT Filed: Feb. 6, 2015

(86) PCT No.: PCT/EP2015/000238
§ 371 (c)(1),
(2) Date: Aug. 9, 2016

(87) PCT Pub. No.: WO2015/124265
PCT Pub. Date: Aug. 27, 2015

(65) Prior Publication Data
US 2016/0354226 A1 Dec. 8, 2016

(30) Foreign Application Priority Data
Feb. 18, 2014 (DE) .................. 10 2014 002 177

(51) Int. Cl.
A61F 5/02 (2006.01)
(52) U.S. Cl.
CPC .............. A61F 5/028 (2013.01); A61F 5/024 (2013.01)

(58) Field of Classification Search
CPC .. A61F 5/026; A61F 5/02; A61F 5/022; A61F 5/024; A61F 5/029; A61F 2005/0132; A61F 2005/0137; A61F 2005/016; A61F 2005/0174; A61F 2005/0179; A61F 2005/0183; A61F 5/03; A63B 21/01181
See application file for complete search history.

(56) References Cited

U.S. PATENT DOCUMENTS 3,351,053 A * 11/1967 Stuttle ................. A61F 5/024
602/19
4,285,336 A * 8/1981 Oebser ................. A61F 5/055
602/19
(Continued)

FOREIGN PATENT DOCUMENTS

CN    104349748 A    2/2015
DE    20204747 U1    7/2002
(Continued)

OTHER PUBLICATIONS

PCT International Search Report for corresponding PCT International Patent Application No. PCT/EP2015/000238, dated Apr. 22, 2015.

Primary Examiner — Kari K Rodriquez
(74) Attorney, Agent, or Firm — Holland & Hart LLP (57) ABSTRACT A trunk orthosis including a bandage that is designed to be put on a patient's trunk, and a supporting device which is connected to the bandage. The supporting device is designed as a frame with frame sections that are hingedly or elastically secured to one another, are spring-biased, and are pre-stressed by the bandage when worn on the patient's trunk.

10 Claims, 7 Drawing Sheets (56) References Cited

U.S. PATENT DOCUMENTS

| | | | | |
|---|---|---|---|---|
| 4,829,989 A * | 5/1989 | Deamer | .................... | A61F 5/02 |
| | | | | 602/19 |
| 7,837,639 B2 * | 11/2010 | Jinright | .................. | A61F 5/026 |
| | | | | 602/16 |
| 8,568,344 B2 * | 10/2013 | Ferguson | ................. | A61H 3/00 |
| | | | | 602/16 |
| 2004/0167449 A1 * | 8/2004 | Heffez | .................... | A61F 5/024 |
| | | | | 602/19 |
| 2005/0228325 A1 | 10/2005 | Zours et al. | | |
| 2008/0208091 A1 | 8/2008 | Vollbrecht et al. | | |
| 2013/0283492 A1 | 10/2013 | Ernst, Jr. et al. | | |
| 2015/0126917 A1 | 5/2015 | Stier | | |
| 2015/0133839 A1 | 5/2015 | Roebelt et al. | | |

FOREIGN PATENT DOCUMENTS

| | | | | |
|---|---|---|---|---|
| DE | 102005031867 A1 | 1/2007 | | |
| DE | 202007008409 U1 | 8/2007 | | |
| DE | 202013000914 U1 | 3/2013 | | |
| DE | 102012009214 A1 | 11/2013 | | |
| EP | 1937194 | 4/2008 | | |
| GB | 1239500 A * | 7/1971 | ............ | A61F 5/024 |
| RU | 2088183 C1 | 8/1997 | | |
| RU | 119998 U1 | 9/2012 | | |
| SU | 173880 A1 | 8/1965 | | |
| WO | 9306798 A2 | 10/1992 | | |
| WO | 2008037584 A1 | 4/2008 | | |
| WO | 2012094499 A1 | 7/2012 | | |

\* cited by examiner

TRUNK ORTHOSIS

TECHNICAL FIELD

The invention relates to a trunk orthosis with a bandage designed to be applied to a patient's trunk, and with a support device connected to the bandage. Such a trunk orthosis is advantageous in particular in cases of stenosis of the vertebral canal and serves to enclose a patient's trunk.

BACKGROUND

It is known to use trunk orthoses to support and relieve the lumbar spine. For example, it may be necessary to relieve a lordosis area of the spine in its entirety, by bridging said area with a support device, resulting in substantial immobilization of the spine in this area. It is also known to support the lumbar area or lumbosacral area of the spine in the event of limited mobility. As the recovery phase progresses, it may be necessary to provide a certain degree of support by means of a bandage or a slightly strengthened bandage.

DE 202 04 747 U1 describes a trunk orthosis which is designed for versatile use in different applications. The bandage has two overlapping constituent bandages, which is intended to allow the bandage height to be adapted to the patient in question. Insertable support rods can be positioned in pockets in order to secure different support devices for bridging or stabilizing the lordosis area. Likewise, an abdominal pad can be provided. The various support devices can be secured on the bandage via hook-and-loop fasteners and can be easily replaced.

DE 10 2005 031 867 A1 relates to a trunk orthosis for enclosing a patient's trunk, with a bandage, and with a support device which is formed by a multiplicity of finger-shaped rods which are arranged next to one another, are oriented in the longitudinal direction of the spine and are connected directly to one another. The finger rods are made of a flexible plastic.

DE 10 2012 009 214 A1 describes a tensioning device for trunk orthoses that engage around the body. The orthosis comprises at least two side parts which are each connected in a tensionable manner via pulleys to a central part arranged in the area of the patient's spine. The side parts and the central part can be composed of several elements arranged above one another.

U.S. Pat. No. 3,351,053 A relates to a back orthosis which, in the front area, encloses the patient's abdomen by means of straps and belts and, in the rear area, has a structure formed by various bows and rods, wherein the elements are connected to one another in a partially articulated manner.

DE 20 2007 008 409 U1 relates to a spinal support appliance which is intended to help a person stand up again after performing a task while kneeling down, by means of a bow, pre-stressed with the aid of rubber bands, applying a standing-up force to the user in the chest area.

WO 93/06798 A2 likewise relates to an aid for standing back up, having two bows which are mounted in the waist area of the user and which exert a resilient restoring force on the user's upper body.

SUMMARY

The object of the present invention is to make available a trunk orthosis which ensures a dynamic hinge function and which at the same time provides the patient with relief in the area of the lumbar spine.

According to the invention, this object is achieved by a back orthosis having the features of the main claim. Advantageous embodiments and developments of the invention are set forth in the dependent claims, the description and the figures.

In the trunk orthosis with a bandage designed to be applied to a patient's trunk, and with a support device connected to the bandage, provision is made that the support device is designed as a frame with frame portions which are mounted on each other in an articulated manner or elastically, and the frame portions are spring-loaded and, in the applied state, are pre-stressed by the bandage. By means of the frame, it is possible to make available a virtually stiff construction, allowing defined forces to be introduced to the patient at the bearing points of the frame or of the frame portions. The articulated or elastic arrangement of the frame portions relative to each other permits a mobility of the spine, while at the same time a supporting effect is achieved. It is thereby possible to relieve the load on vertebrae, in particular lumbar vertebrae or lower thoracic vertebrae. The load can be relieved, for example, by the bandage element being placed tightly around the trunk such that a tensile force is applied to the frame or the frame portions. The frame portions are then pre-stressed by the tensile force and have the effect, for example, that flexion is assisted and the intervertebral area of the lumbar spine is partially widened. The bandage is advantageously guided ventrally, i.e. placed around the abdomen, while the frame is guided dorsally. The frame portions can have a double C shape if the hinge or the elastic bending point between the frame portions is arranged approximately in a frontal plane lying in front of the spine or at the height of the spine. The bandage is not guided completely around the trunk; instead it is sufficient if the bandage is present only in the frontal abdominal area, with the frame forming the closure to the rear. The frame can be designed in one piece, such that the frame portions are movable relative to each other elastically. The elastic restoring forces are applied by the frame upon deformation on account of the tensioning of the bandage about the trunk. In a multi-part design of the frame, the frame portions can be designed as frame elements which can be produced separately from each other and can be mounted on each other. The mounting can be effected reversibly by plug systems or other form-fit connections or can be effected permanently by adhesive bonding, soldering or welding. If the frame portions consist of several frame elements, there is also the possibility of adapting the frame elements individually to the user. The frame elements can be designed to be adjustable and to be fixed on each other. In particular, with a division in the sagittal plane, there is the possibility of the width of the orthosis being adaptable to the respective patient, for example by screw sleeves or plug sleeves or intermediate pieces that can be used to adjust the width. The frame elements themselves and also the connecting element can be elastic in order to permit a certain flexibility and adaptability to the user and to the conditions of use.

The frame portions or frame elements are mounted with spring loading relative to each other, wherein the spring can serve as a force limiter. The spring characteristic can be linear, progressive or degressive. The spring force is adjustable, such that the degree of force applied to the respective patient is adjustable. Advantageously, the frame portions or frame elements are spring-loaded relative to each other in such a way that, after the trunk orthosis has been applied, a widening takes place in the area of the lumbar spine, particularly in the lower and middle areas of the lumbar spine. If the frame is designed in one piece, the spring action between the upper and lower frame portion, i.e. the transverse portion bearing in the lower thoracic area and the pelvic area, is made available via an elastic portion or elastic portions to the lateral areas of the orthosis, for example through a winding such as in a helical or spiral spring. For this purpose, it is advantageous if the frame element of the frame is produced from a solid material. If the orthosis has a multi-part design, the spring force can be made available by separate springs or spring elements, which are secured on the frame portions. Separate spring elements have the advantage of being easier to produce and easier to change and adapt, so as to be able to provide the desired spring force for the respective patient.

The frame portions or frame elements can be mounted on hinge mechanisms which are positioned medially and laterally with respect to the trunk. The hinge mechanisms can be designed, for example, as separate components in which a spring is integrated, the pre-stressing of the spring being adjustable. Seats for the frame elements or frame portions can be provided on the hinge mechanisms, such that replaceability is possible at the hinge mechanisms for the purpose of adaptation to the respective patients. Alternatively, provision is made that the frame portions or frame elements are adjustable, for example in height and/or width, such that the frame structure, once constructed, can subsequently be adjusted for all patients. The height of the frame elements relative to the hinge mechanisms can be obtained by suitably securing the frame elements on the hinge mechanisms.

Advantageously, the frame portions or frame elements are designed as a tube structure, resulting in a particularly light structure with a high degree of stability. It is thereby possible to provide a virtually stiff frame structure so as to be able to easily transmit the forces that are to be applied to the patient. If no separate hinge mechanisms with a rigid axis are provided, the hinge mechanism can also be effected by a displaceable arrangement of the frame portions or frame elements relative to each other on the bandage parts or on the bandage, wherein the spring force is applied by the bandage itself and the bandage at the same time serves to secure the frame elements to each other.

Cushioning elements can be arranged on the frame portions so as to allow the frame elements or frame portions to be supported, in a manner comfortable for the patient, in the area of the sacrum or in the lumbosacral area and also in the upper area of the lumbar spine or in the lower area of the thoracic spine.

The bandage can have a multi-part design and have at least two bandage elements, which can be secured to each other via securing means. The securing means serve in particular for form-fit engagement of the bandage elements on each other and can be designed as hook-and-loop fasteners, buckles, hooks, clips, studs or the like.

Advantageously, the bandage is made from a flexible material in order to facilitate application of the trunk orthosis. If the material is elastic, the bandage can also serve for a resilient and pre-stressed bearing on the patient.

A tightening strap can be secured on the support device and is advantageously guided on or in the bandage. After the trunk orthosis has actually been applied, it is thereby possible to apply a desired pre-stressing by the closure of the two bandage elements to the front of the body. For this purpose, the tightening strap can be designed as a pulley system and is advantageously secured on the bandage, for example by a hook-and-loop fastener which is arranged at the end of the tightening strap. By means of the tightening strap being deflected a number of times on the bandage, an increase in force can be obtained without the application of the force being taxing for the user. The tightening strap can be secured or guided on the hinge, the hinge mechanism or in the area of the hinge of the frame elements. The tensile force provided by the tightening strap is advantageously applied through the hinge axis or in the area of the hinge axis. It is likewise possible to secure the tightening strap directly on the hinge mechanism or to guide it there through a deflection device, for example a ring or a D-ring. Other guide means on the hinge mechanism are likewise possible in order to obtain a defined introduction of force in the area of the hinge axis, thereby ensuring exact introduction of force and, consequently, efficacy of the frame elements at the respective bearing points. If no hinge is formed between the frame portions, it is possible, by assigning the tightening strap to the frame via passages or guide elements, that the introduction of force permanently takes place at the desired location.

The spring elements for the pre-stressing of the frame portions or frame elements relative to each other can be designed as leg springs or bar springs. The springs can be provided with stops which are adjustable, so as to obtain, on the one hand, a limitation of force and, on the other hand, a limitation of movement. In this way, desired movements or extents of movement can also be restricted.

BRIEF DESCRIPTION OF THE DRAWINGS

Illustrative embodiments of the invention are explained in more detail below with reference to the figures, in which.

DETAILED DESCRIPTION

Figure 1:
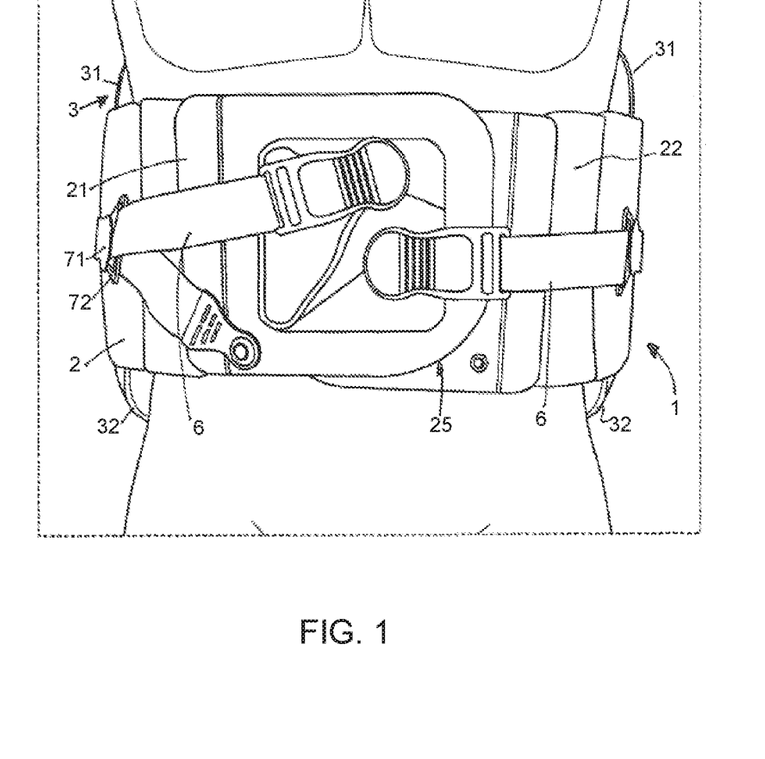
FIG. 1 shows a front view of a first embodiment.

FIG. 1 shows a front view of an orthosis 1 applied to a patient's trunk. At the front, the trunk orthosis 1 has a bandage 2 composed of several bandage elements 21, 22. The bandage elements 21, 22 themselves can consist of several components which are arranged on one another releasably or fixedly. The bandage elements 21, 22 are arranged to the left and right of the trunk on a frame 3, which has an upper frame portion 31 and a lower frame portion 32. To apply the trunk orthosis 1, the two bandage elements 21, 22 are opened, the frame 3 is applied to the back, and the bandage elements 21, 22 are then secured to each other via securing means 25 which, in the illustrative embodiment shown, are designed as hook-and-loop fasteners. In this way, the trunk orthosis 1 encloses the patient's body all the way around but the bandage elements 21, 22 are only arranged in the area of the abdomen. After the two bandage elements 21, 22 have been laid one over the other and have been secured by form-fit engagement, for example via a hook-and-loop fastener 25, the frame 3 presses with the upper frame portion 31 and the lower frame portion 32 against the back and against the pelvis, respectively, at their supporting points. In order to increase this pressure, tightening straps 6 are arranged on the front of the trunk orthosis 1 and can be secured on the upper bandage portion 21. After the bandage elements 21, 22 have been closed, the securing is advantageously effected via a hook-and-loop fastener, in order to achieve an almost stepless adaptation of the pressing force by adjusting the length or position of the tightening straps 6. The left-hand tightening strap 6 in the view in FIG. 1 is secured with its first end on the lower edge of the bandage element 21, is then guided through an eye 72, which is secured on a tab 71 on the 3, and is then guided back onto the bandage element 21 and secured there on a fleeced area by means of a hook area of a hook-and-loop fastener. By means of this deflection, an increased tensile force can be achieved, at the same time with precise introduction of the forwardly pulling force by the tightening strap 6. The right-hand tightening strap 6 in the view is simply secured on a correspondingly shaped tab on the frame 3 and is fixed on the front of the upper bandage element 21 via a hook-and-loop fastener.

Figure 2:
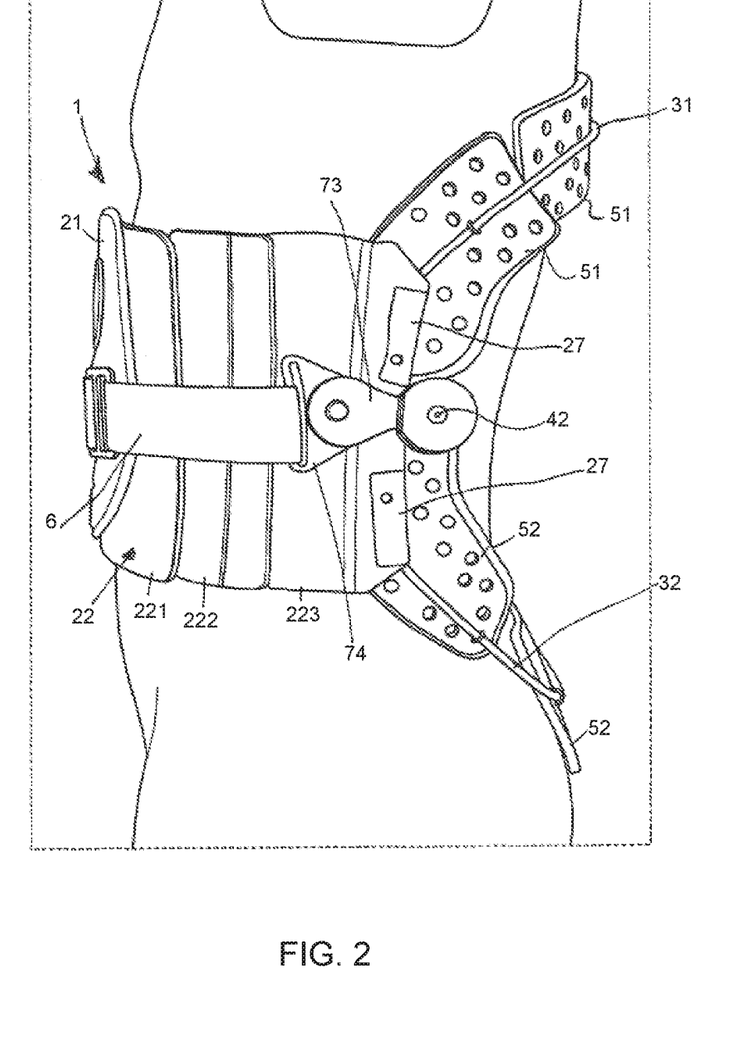
FIG. 2 shows a side view of FIG. 1.

FIG. 2 shows a side view of the trunk orthosis 1 according to the illustrative embodiment in FIG. 1. It will be seen that the bandage element 22 is composed of three individual components 221, 222, 223 which can be secured on a, for example via a large number of hook-and-loop fasteners. It is thereby possible to obtain a modular configuration of the bandage 2 in order to provide adjustments in length. With its rear part 223, the bandage element 22 is secured via tabs 27 on the two frame portions 31, 32 designed as separate frame elements. The frame elements 31, 32 are designed as a tube structure with a round tube cross section, in particular with a hollow cross section, in order to obtain a design that is light and at the same time stable and, if appropriate, elastically resilient. In order to position the orthosis on the body, a first tensile force is applied via the tabs 27 and via the frame elements 31, 32 in the frontal direction and, therefore, a slight pressure is also applied to the patient's back and pelvis.

Cushioning elements 51, 52 or also pads, arranged on the frame elements 31, 32, distribute forces and increase the comfort with which the frame elements 31, 32 bear on the body. The cushioning elements 51, 52 provide cushioning both in the area of the thoracic spine and also in the area of the lumbar spine, and also laterally on the trunk. The frame portions 31, 32 run in a double C shape and initially extend upward and downward, respectively, in a straight line from the point of connection of the two frame portions 31, 32 and run in a double arc, which runs both from the top downward and from the bottom upward and from front to rear, to the connection point on the other side.

The two frame portions 31, 32 are mounted pivotably on each other on a hinge mechanism 42. A corresponding hinge mechanism is likewise provided on the other side and permits substantially free pivoting of the frame elements 31, 32 about the hinge mechanism 42. By way of a tab 73, and an eye 74 mounted thereon in an articulated manner, the tightening strap 6 is tensioned frontally, and a force acting centrally on the pivot axis of the hinge mechanism 42 permits precise introduction of force into the hinge area. The greater part of the effective force exerted on the back and the pelvis is exerted via the tightening strap 6 and the tabs 73, which are guided laterally on the body. By way of the tab 73, the tightening strap 6 acts directly on the hinge area and pulls forward the hinge area substantially in the middle between the upper transverse arc and the lower transverse arc.

Figure 3:
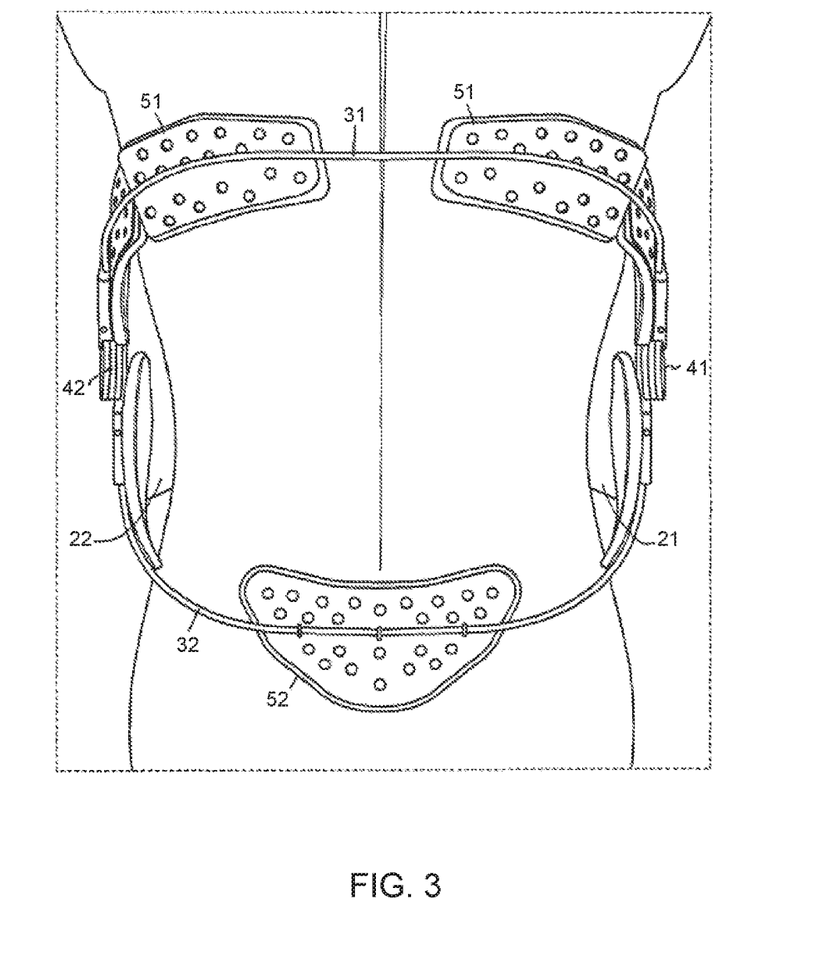
FIG. 3 shows a rear view of FIG. 1.

FIG. 3 shows the orthosis 1 in a rear view depicting the two separately produced frame elements 31, 32, the upper cushioning elements 51 in the area of the thoracic spine, the lower cushioning element 52 in the area of the lumbar spine, and also the lateral cushioning elements. Instead of or in addition to the cushioning elements, it is also possible for pads to be secured on the frame or the frame elements. The frame elements 31, 32 are mounted pivotably on each other on both sides via hinge mechanisms 41, 42 and are applied around the patient's body via the tightening straps 6 (not shown) and bandage elements 21, 22. The orthosis 1 is thus designed closed circumferentially about the patient's trunk. The hinge mechanisms 41, 42 can be provided with springs, for example compression springs, tension springs, spiral springs or elastomer elements, so as to be able to be pre-stressed relative to each other. The spring force advantageously acts such that bending forward is assisted, i.e. a forwardly acting force is present in the area of the thoracic spine and the area of the lumbar spine. As an alternative to a separate spring element, it is possible to connect the frame elements 31, 32 to each other such that an elastic pre-stressing force prevails. It is likewise possible for the frame 3 to be designed in one piece and, by a suitable configuration of the frame portions 31, 32, to achieve the desired effect of flexion in the frontal direction.

Figure 4:
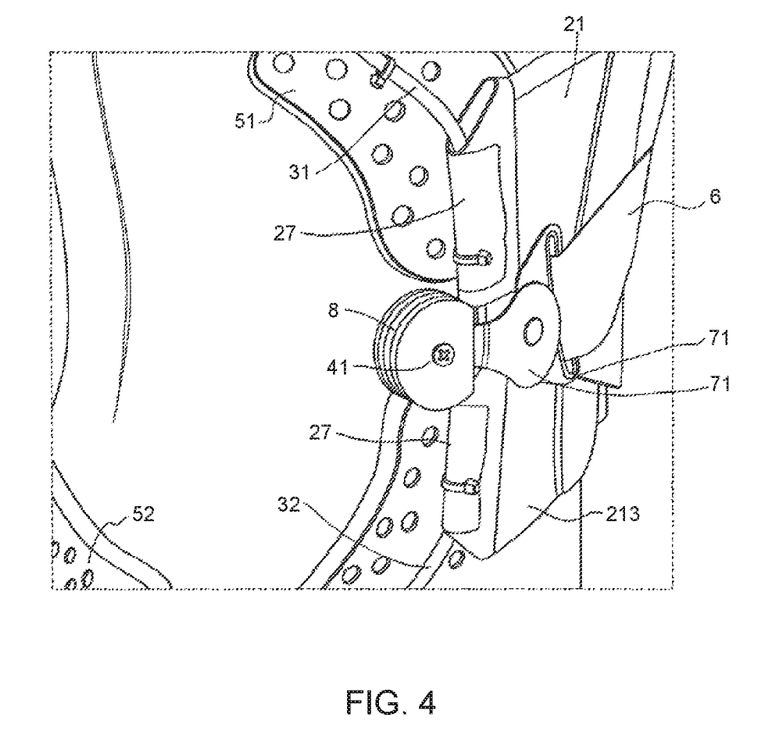
FIG. 4 shows a detailed view.

FIG. 4 shows a detailed view of the orthosis in the area of the point of connection of the two frame elements 31, 32. The tabs 27 of the rear bandage element 213 are secured on the frame elements 31, 32, likewise the tab 71 in the area of the pivot point of the hinge mechanism 41. An eye 72 is secured pivotably on the tab 71 and serves to deflect the tightening strap 6. A torsion spring 8 is arranged inside the hinge mechanism 41 in order to load the two frame elements 31, 32 in the desired direction, to load them in the frontal direction in the illustrative embodiment shown, so as to achieve a bending and widening of the vertebral canal. The tabs 27 can be secured on the frame elements 31, 32 via reversible fastening elements such as hook-and-loop fasteners, press studs or the like; it is also possible in principle to provide a permanent connection by welding, sewing or, for example, cable ties.

Figure 5:
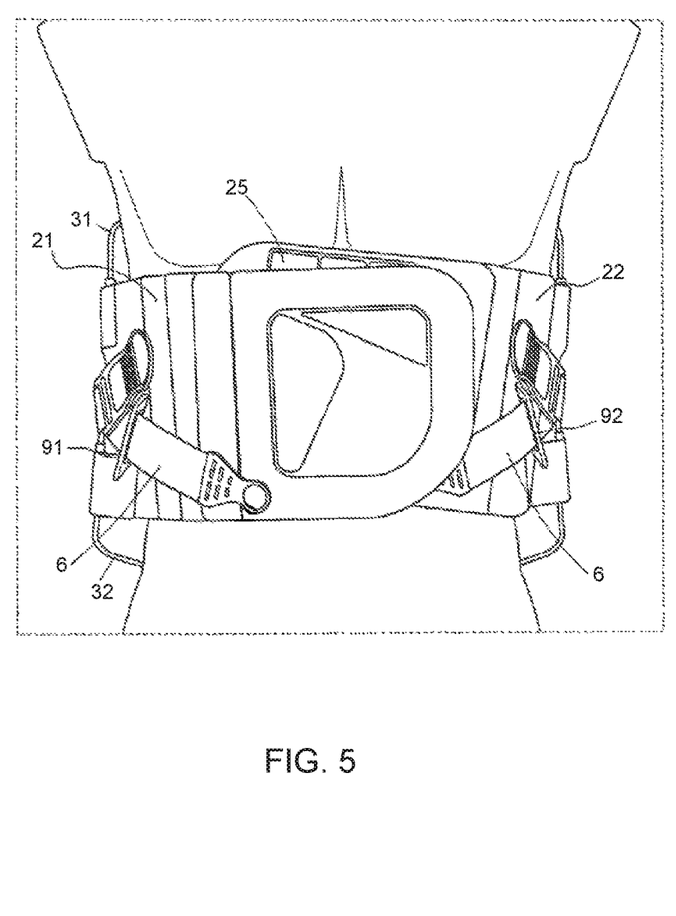
FIG. 5 shows a front view of a variant.

FIG. 5 shows a variant of the invention in which the securing means 25 are shown in the form of hook-and-loop fasteners; it will also be noted that both tightening straps 6 are mounted on the respective connections or in the middle between the frame portions 31, 32 via deflection devices of the kind shown in detail in FIG. 4, in order to achieve a pulley-like construction. It is thereby possible to achieve an increase in force when the tightening straps 6 are drawn and are secured frontally on fleeced areas on the top of the bandage element 21.

Figure 6:
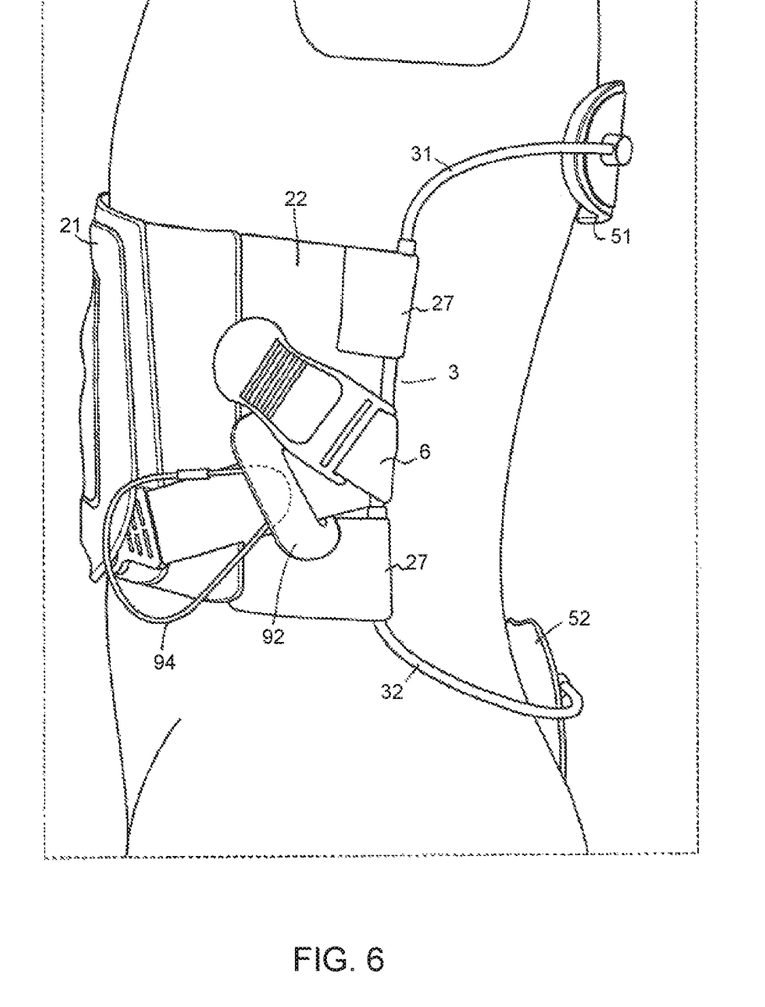
FIG. 6 shows a side view of the variant according to FIG. 5.

Slides 91, 92, which are explained in more detail with reference to FIG. 6, are arranged on the tightening straps 6.

FIG. 6 shows a side view of the orthosis according to FIG. 5 and illustrates that the frame portions 31, 32 are mounted elastically on each other without a hinge-like mechanism, either via a plug system, for example an elastic connecting rod, or by sleeves secured or formed on the frame portions 31, 32. The bandage element 22 is secured on the frame portions 31, 32 via the tabs 27; between the tabs 27 a free space is formed through which the tightening strap 6 is guided, so as to ensure a spatial assignment of the deflection point of the tightening strap 6. Force is introduced centrally at the point of deflection of the tightening strap 6 which is guided through behind the frame 3 and then secured on the front of the bandage elements 21, 22, for example via hook-and-loop fasteners. The slide 92 is provided with a loop 94, by way of which it is possible to obtain an improved grip, in order to exert tensioning forces on the tightening strap 6.

Figure 7:
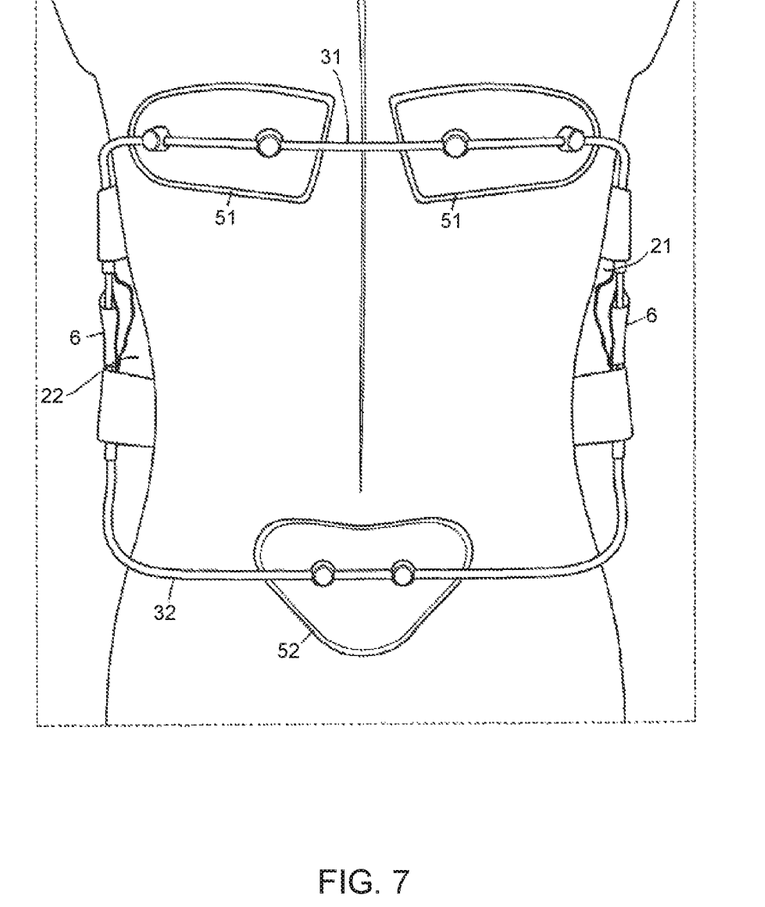
FIG. 7 shows a rear view of the variant according to FIG. 5.

FIG. 7 shows the rear of the orthosis with two upper cushioning elements 51, which are arranged to both sides of the spine, and with a lower cushioning element 52, which lies on the patient in the area of the sacrum. It will be seen that the tightening straps 6 are placed around the frame 3 in the area between the upper and lower frame portions 31, 32.

The invention claimed is:

1. A trunk orthosis, comprising:
   a bandage designed to be applied ventrally to a patient's trunk;
   a support device connected to the bandage and designed to be applied dorsally to the patient's trunk, the support device being designed as a frame with frame portions, the frame portions mounted on each other in an articulated manner or elastically with a hinge, the frame portions being spring-loaded and, in an applied state, being pre-stressed by the bandage, the frame portions including an upper frame part configured to be supported in the area of the patient's thoracic spine and a lower frame part configured to be supported in the area of the patient's lumbar spine;
   at least one tightening strap secured to or guided on the hinge and secured to the bandage, the at least one tightening strap being tensioned frontally and configured to apply a force centrally to a pivot axis of the hinge.

2. The trunk orthosis as claimed in claim 1, wherein the frame portions are mounted on the hinge includes first and second hinge mechanisms which are positioned medially and laterally with respect to the trunk.

3. The trunk orthosis as claimed in claim 1, wherein cushioning elements or pads are arranged on the frame portions.

4. The trunk orthosis as claimed in claim 1, wherein the bandage has a multi-part design and has at least two bandage elements, which can be secured to each other via a securing means.

5. The trunk orthosis as claimed in claim 4, wherein the securing means are designed as form-fit elements.

6. The trunk orthosis as claimed in claim 1, wherein the bandage is made from a flexible and/or elastic material.

7. The trunk orthosis as claimed in claim 1, wherein the at least one tightening strap is guided on the bandage.

8. The trunk orthosis as claimed in claim 1, wherein the at least one tightening strap is designed as a pulley system.

9. The trunk orthosis as claimed in claim 1, wherein the at least one tightening strap can be secured reversibly on the bandage.

10. The trunk orthosis as claimed in claim 1, wherein the support device has a multi-part design.

* * * * *